(12) United States Patent
Trah

(10) Patent No.: US 6,638,940 B1
(45) Date of Patent: Oct. 28, 2003

(54) TETRAHYDROPYRIDINES AS PESTICIDES

(75) Inventor: Stephan Trah, Freiburg im Breisgau (DE)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/069,807

(22) PCT Filed: Sep. 1, 2000

(86) PCT No.: PCT/EP00/08566

§ 371 (c)(1),
(2), (4) Date: Feb. 25, 2002

(87) PCT Pub. No.: WO01/17964

PCT Pub. Date: Mar. 15, 2001

(30) Foreign Application Priority Data

Sep. 3, 1999 (CH) .............................................. 1607/99

(51) Int. Cl.$^7$ ........................ A01N 43/40; C07D 211/70
(52) U.S. Cl. ........................ 514/277; 514/352; 514/357; 514/358; 546/329; 546/330; 546/333; 546/339; 546/340; 546/342; 546/343
(58) Field of Search .................................. 514/277, 352, 514/357, 358; 546/329, 330, 333, 339, 340, 342, 343

(56) References Cited

U.S. PATENT DOCUMENTS

| 4,485,107 A | 11/1984 | Kennis et al. |
|---|---|---|
| 5,569,664 A | 10/1996 | Silverman et al. |
| 5,639,763 A | 6/1997 | Silverman et al. |

FOREIGN PATENT DOCUMENTS

| GB | 2 319 524 | 5/1998 |
|---|---|---|
| WO | WO 98/00015 | 8/1988 |
| WO | WO 94/07857 A | 4/1994 |
| WO | WO 95/23507 | 9/1995 |
| WO | WO 96/36228 | 11/1996 |
| WO | WO 97/45423 A | 12/1997 |

OTHER PUBLICATIONS

Sathe, Dhananjay G. et al.: "Synthesis of 3,5–lutidine by catalytic transger hydrogenation via 1,2,5,6–tetrahydropyridine", Indian J. Chem., Sect. B: Org. Vhem. Incl. Med. Chem. (1994), 33B(10), 986–7.

*Primary Examiner*—Patricia L. Morris
(74) *Attorney, Agent, or Firm*—Rose M. Allen

(57) ABSTRACT

Compounds of formula (I)

are described, wherein $R_1$ and $R_2$ are for example, independently of each other, halogen, $C_1$–$C_6$-alkyl, $C_3$–$C_6$-cycloalkyl, halogen-$C_1$–$C_6$-alkyl, halogen-$C_3$–$C_6$-cycloalkyl, $C_2$–$C_4$-alkenyl, $C_2$–$C_4$-alkinyl, halogen-$C_2$–$C_4$-alkenyl and halogen-$C_2$–$C_4$-alkinyl;

$R_3$ is hydrogen, OH, halogen, $C_1$–$C_6$-alkoxy, or —O—C(=O)—$C_1$–$C_6$-alkyl;

$R_4$ is for example phenyl, benzyl, phenoxy or benzyloxy, which is substituted by substituents selected from the group consisting of halogen, cyano, $NO_2$, $C_1$–$C_6$-alkyl, $C_3$–$C_8$-cycloalkyl, $C_3$–$C_8$-cyclalkyl-$C_1$–$C_6$-alkyl, halogen-$C_1$–$C_6$-alkyl, $C_1$–$C_6$-alkoxy, $C_3$–$C_8$-cycloalkoxy, $C_3$–$C_8$-cycloalkoxy-$C_1$–$C_6$-alkoxy, $C_3$–$C_8$-cycloalkoxy-$C_1$–$C_6$-alkoxy, halogen-$C_1$–$C_6$-alkoxy, $C_2$–$C_4$-alkenyl, $C_2$–$C_4$-alkinyl, halogen-$C_2$–$C_4$-alkenyl, halogen-$C_2$–$C_4$-alkinyl, $C_2$–$C_6$-alkenyloxy, $C_2$–$C_6$-alkinyloxy, halogen-$C_2$–$C_6$-alkenyloxy, halogen-$C_2$–$C_6$-alkenyloxy, —$NR_6$—C(=O)—O—$C_1$–$C_6$-alkyl, —$NR_6$—C(=O)—O-halogen-$C_1$–$C_6$-alkyl, —C($R_7$)=N—W—$R_8$, phenyl, benzyl, phenoxy, benzyloxy, heterocycyl and heterocyclyoxy;

the two $R_5$ independently of one another, are hydrogen or $C_1$–$C_6$-alkyl;

$R_6$ is hydrogen, $C_1$–$C_6$-alkyl or benzyl;

$R_7$ is for example halogen or $C_1$–$C_6$-alkyl;

$R_8$ is for example hydrogen or $C_1$–$C_6$-alkyl;

m is 0, 1, 2, 3, 4 or 5; n is 0, 1, 2, 3, 4 or 5; p is 0, 1 or 2; q is 0 or 1;

W is O or NH or N—$C_1$–$C_6$-alkyl;

a method of producing and the use of these compounds, pesticides whose active ingredient is selected from these compounds or from an agrochemically employable salt thereof, a method of producing and the use of these compositions, plant propagating material that has been treated with these compositions and a method of controlling pests.

6 Claims, No Drawings

TETRAHYDROPYRIDINES AS PESTICIDES

The object of the present invention is a compound of formula

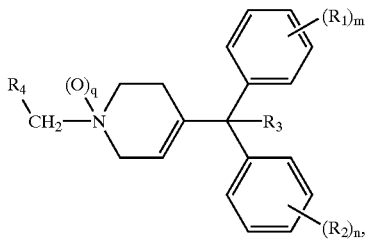

(I)

wherein $R_1$ and $R_2$, independently of one another, are halogen, $C_1$–$C_6$-alkyl, $C_3$–$C_6$-cycloalkyl, halogen-$C_1$–$C_6$-alkyl, halogen-$C_3$–$C_6$-cycloalkyl, $C_2$–$C_4$-alkenyl, $C_2$–$C_4$-alkinyl, halogen-$C_2$–$C_4$-alkenyl, halogen-$C_2$–$C_4$-alkinyl, $C_1$–$C_6$-alkoxy, halogen-$C_1$–$C_6$-alkoxy, $C_2$–$C_6$-alkenyloxy, $C_2$–$C_6$-alkinyloxy, halogen-$C_2$–$C_6$-alkenyloxy, halogen-$C_2$–$C_6$-alkinyloxy, —$SF_5$, —$C(=O)N(R_5)_2$, —O—$C(=O)N(R_5)_2$, —CN, —$NO_2$, —$S(=O)_2N(R_5)_2$, —$S(=O)_p$—$C_1$–$C_6$-alkyl, —$S(=O)_p$-halogen-$C_1$–$C_6$-alkyl, —O—$S(=O)_p$—$C_1$–$C_6$-alkyl, —O—$S(=O)_p$-halogen-$C_1$–$C_6$-alkyl, phenyl, benzyl, phenoxy or benzyloxy, wherein each of the phenyl, benzyl, phenoxy or benzyloxy radicals is either un-substituted or mono- to penta-substituted in the aromatic ring, independently of each other, by substituents selected from the group consisting of halogen, cyano, $NO_2$, $C_1$–$C_6$-alkyl, halogen-$C_1$–$C_6$-alkyl, $C_1$–$C_6$-alkoxy and halogen-$C_1$–$C_6$-alkoxy;

$R_3$ is hydrogen, OH, halogen, $C_1$–$C_6$-alkoxy, or —O—C(=O)—$C_1$–$C_6$-alkyl;

$R_4$ is $C_1$–$C_6$-alkyl, halogen-$C_1$–$C_6$-alkyl, $C_3$–$C_6$-cycloalkyl, halogen-$C_3$–$C_6$-cycloalkyl, $C_3$–$C_6$-cycloalkoxy, halogen-$C_1$–$C_6$-alkoxy, $C_2$–$C_4$-alkenyl, $C_2$–$C_4$-alkinyl, halogen-$C_2$–$C_4$-alkenyl, halogen-$C_2$–$C_4$-alkinyl, $C_1$–$C_6$-alkoxy, halogen-$C_1$–$C_6$-alkoxy, $C_2$–$C_6$-alkenyloxy, $C_2$–$C_6$-alkinyloxy, halogen-$C_2$–$C_6$-alkenyloxy, halogen-$C_2$–$C_6$-alkinyloxy, —C(=O)—$C_3$–$C_6$-alkyl, —C(=O)-halogen-$C_1$–$C_6$-alkyl, —C(=O)—O$C_1$–$C_6$-alkyl, —C(=O)—O-halogen-$C_1$–$C_6$-alkyl, —$NR_6$—C(=O)—O—$C_1$–$C_6$-alkyl, —$NR_6$—C(=O)—O-halogen-$C_1$–$C_6$-alkyl, —C(=O)N(R_5)_2$, —O—C(=O)N(R_5)_2$, —CN, —$NO_2$, —$S(=O)_2N(R_5)_2$, —$S(=O)_p$—$C_1$–$C_6$-alkyl, —$S(=O)_p$-halogen-$C_1$–$C_6$-alkyl, —O—$S(=O)_p$—$C_1$–$C_6$-alkyl, —O—$S(=O)_p$-halogen-$C_1$–$C_6$-alkyl; benzyl, phenoxy, benzyloxy; or phenyl, benzyl, phenoxy or benzyloxy which is mono- to penta-substituted, independently of each other, by substituents selected from the group consisting of halogen, cyano, $NO_2$, $C_1$–$C_6$-alkyl, $C_3$–$C_8$-cycloalkyl, $C_3$–$C_8$-cycloalkyl-$C_1$–$C_6$-alkyl; halogen-$C_1$–$C_6$-alkyl, $C_1$–$C_6$-alkoxy, $C_3$–$C_8$-cycloalkoxy, $C_3$–$C_8$-cycloalkoxy-$C_1$–$C_6$-alkyl, $C_3$–$C_8$-cycloalkyl-$C_1$–$C_6$-alkoxy, halogen-$C_1$–$C_6$-alkoxy, $C_2$–$C_4$-alkenyl, $C_2$–$C_4$-alkinyl, halogen-$C_2$–$C_4$-alkenyl, halogen-$C_2$–$C_4$-alkinyl, $C_2$–$C_6$-alkenyloxy, $C_2$–$C_6$-alkinyloxy, halogen-$C_2$–$C_6$-alkenyloxy, halogen-$C_2$–$C_6$-alkinyloxy, —$NR_6$—C(=O)—O—$C_1$–$C_6$-alkyl, —$NR_6$—C(=O)—O—$C_2$–$C_6$-alkenyl, —$NR_6$—C(=O)—O-halogen-$C_1$–$C_6$-alkyl, —C($R_7$)=N—W—$R_8$, phenyl, benzyl, phenoxy, benzyloxy, heterocyclyl and heterocyclyloxy, wherein, depending on the substitution possibility on the ring, the heterocyclyl and heterocyclyloxy radicals are optionally mono- to trisubstituted by substituents selected from the group consisting of halogen, $C_1$–$C_6$-alkyl, halogen-$C_1$–$C_6$-alkyl, $C_1$–$C_6$-alkoxy, halogen-$C_1$–$C_6$-alkoxy, $C_3$–$C_6$-cycloalkyl-$C_1$–$C_6$-alkyl, cyano-$C_1$–$C_6$-alkyl, $C_3$–$C_6$-alkenyl, $C_3$–$C_6$-alkinyl, phenyl or benzyl;

the two $R_5$ independently of one another, are hydrogen or $C_1$–$C_6$-alkyl;

$R_6$ is hydrogen, $C_1$–$C_6$-alkyl or benzyl;

$R_7$ is halogen, $C_1$–$C_6$-alkyl, $C_3$–$C_8$-cycloalkyl, $C_3$–$C_8$-cycloalkyl-$C_1$–$C_6$-alkyl, halogen-$C_1$–$C_6$-alkyl, $C_1$–$C_6$-alkoxy, $C_3$–$C_8$-cycloalkoxy, $C_3$–$C_8$-cycloalkoxy-$C_1$–$C_6$-alkyl, halogen-$C_1$–$C_6$-alkoxy —NH($C_1$–$C_6$-alkyl) or —N($C_1$–$C_6$-alkyl)$_2$;

$R_8$ is hydrogen, $C_1$–$C_6$-alkyl, $C_3$–$C_8$-cycloalkyl, $C_3$–$C_8$-cycloalkyl-$C_1$–$C_6$-alkyl, halogen-$C_1$–$C_6$-alkyl or —C(=O)—$C_1$–$C_6$-alkyl;

m is 0, 1, 2, 3, 4 or 5;

n is 0, 1, 2, 3, 4 or 5;

p is 0, 1 or 2;

q is 0 or 1

W is O or NH or N—$C_1$–$C_6$-alkyl;

and, if appropriate, the E/Z isomers, E/Z isomeric mixtures and/or tautomers thereof, each in free form or in salt form;

a method of producing and the use of these compounds, pesticides whose active ingredient is selected from these compounds or from an agrochemically employable salt thereof, a method of producing and the use of these compositions, plant propagating material that has been treated with these compositions and a method of controlling pests.

In the literature, certain piperidine derivatives have been proposed as active ingredients in pesticides. The biological properties of these known compounds, however, are not fully satisfactory in the field of pest control, which is why there is a need to produce further compounds with pesticidal properties, especially for the control of insects and members of the order Acarina; this problem is solved according to the invention with the development of the present compounds of formula (I).

The compounds of formula (I) and where appropriate their tautomers can form salts, for example acid addition salts. These are formed for example with strong inorganic acids, typically mineral acids, e.g. sulphuric acid, a phosphoric acid or a hydrohalic acid, or with strong organic carboxylic acids, typically $C_1$–$C_4$alkanecarboxylic acids substituted where appropriate for example by halogen, e.g. acetic acid, such as optionally unsaturated dicarboxylic acids, e.g. oxalic, malonic, maleic, fumaric or phthalic acid, such as hydroxy-carboxylic acids, e.g. ascorbic, lactic, malic, tartaric or citric acid, or benzoic acid, or with organic sulphonic acids, typically $C_1$–$C_4$alkane or arylsulphonic acids substituted where appropriate for example by halogen, e.g. methane- or p-toluene-sulphonic acid. In a broader sense, compounds of formula (I) with at least one acid group can form salts with bases. Suitable salts with bases are for example metal salts, such as alkali or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl, diethyl, triethyl or dimethylpropylamine, or a mono-, di- or trihydroxy-lower alkylamine, e.g. mono-, di- or triethanolamine. Corresponding internal salts where appropriate may also be formed. The free form is preferred on the one hand. Of the salts of compounds of formula (I), the agrochemically beneficial salts are preferred. Hereinbefore and hereinafter, the free compounds of formula (I) or their salts are understood where appropriate to include also the corresponding salts, or the salts are understood to include also the free compounds of formula (I). The same applies to tautomers of compounds of formula (I) and salts thereof. Unless otherwise defined, the general terms used hereinabove and hereinbelow have the meanings given hereinbelow.

Halogen—as a group per se or as structural element of other groups and compounds such as haloalkyl, halocycloalkyl, haloalkenyl, haloalkinyl and haloalkoxy—is fluorine, chlorine, bromine or iodine, in particular fluorine, chlorine or bromine, mainly fluorine or chlorine, especially chlorine.

If not otherwise defined, carbon-containing groups and compounds each contain 1 to 20, inclusively, preferably 1 to 18, in particular 1 to 10, especially 1 to 6, in particular 1 to 4, especially 1 to 3, particularly 1 or 2, carbon atoms, with methyl being preferred in particular.

Alkyl—as a group per se and as structural element of other groups and compounds such as haloalkyl, alkoxy, alkoxyalkyl, haloalkoxy, alkoxycarbonyl, alkylthio, haloalkylthio, alkylsulphonyl and alkylsulphonyloxy—is, in each case with due consideration of the specific number of carbon atoms in the group or compound in question, either straight-chained, e.g. methyl, ethyl, n-propyl, n-butyl, n-hexyl, n-octyl, n-decyl, n-dodecyl, n-hexadecyl or n-octadecyl, or branched, for example isopropyl, isobutyl, sec-butyl, tert-butyl, isopentyl, neopentyl or isohexyl.

Alkenyl and alkinyl—as groups per se and as structural elements of other groups and compounds, such as of haloalkenyl, haloalkinyl, alkenyloxy, haloalkenyloxy, alkinyloxy or haloalkinyloxy—are straight-chained or branched and respectively contain two or preferably one unsaturated carbon-carbon bond(s). Vinyl, prop-2-en-1-yl, 2-methylprop-2-en-1-yl, but-2-en-1-yl, but-3-en-1-yl, prop-2-in-1-yl, but-2-in-1-yl and but-3-in-1-yl may be mentioned of example.

Cycloalkyl—as a group per se and as a structural element of other groups and compounds, for example of alkyl—is cyclopropyl, cyclobutyl, cyclopentyl, cyclohexyl, cycloheptyl and cyclooctyl. Cyclopentyl and cyclohexyl are preferred, in particular cyclopropyl.

Halogen-substituted carbon-containing groups and compounds, such as haloalkyl and haloalkoxy, can be partially halogenated or perhalogenated, in the case of polyhalogenation it being possible for the halogen substituents to be identical or different. Examples of haloalkyl—as a group per se and as structural element of other groups and compounds such as haloalkoxy,—are methyl which is mono- to trisubstituted by fluorine, chlorine and/or bromine, such as $CHF_2$, $CF_3$ or $CH_2Cl$; or ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $_{CH2}CH_2Cl$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$, $CF_2CF_2CF_3$, $CH(CF_3)_2$ or $CH_2CH_2CH_2Cl$; and butyl or one of to nona-substituted by fluorine, chlorine and/or bromine, such as $CF(CF_3)CHFCF_3$, $CF_2(CF_2)_2CF_3$ oder $CH_2(CF_2)_2CF_3$.

Aryl signifies especially phenyl or naphthyl, preferably phenyl.

Heterocyclyl signifies a 5 to 7-membered, saturated or unsaturated, preferably aromatic ring with one to four hetero atoms selected from the group consisting of N, O and S. Preference is given to aromatic 5 and 6-rings that have one nitrogen atom as a hetero atom and optionally one further hetero atom, preferably nitrogen or sulphur, especially nitrogen. Preferred heterocyclyl radicals are for example pyrrolyl, pryazolyl, imidazolyl, 1,2,4-triazolyl, tetrazolyl, pyrazinyl, pyridyl, pyrimidinyl, pyridazinyl, thiazolyl, isothiazolyl, isoxazolyl, indolyl, indazolyl, benzimidazolyl, benzothiazolyl, furanyl, tetrahydrofuranyl and thienyl; tetrazolyl is preferred, especially tetrazolyl which is substituted by $C_1$–$C_3$-alkyl, particularly methyl, ethyl, propyl or isopropyl, especially ethyl.

Preferred embodiments in terms of the invention are compounds of formula (I), wherein a) $R_1$ and $R_2$, independently of one another, are halogen, $C_1$–$C_2$-alkyl, $C_3$–$C_6$-cycloalkyl, halogen-$C_1$–$C_2$-alkyl, $C_1$–$C_2$-alkoxy, halogen-$C_1$–$C_2$-alkoxy, —C(=O)N(CH$_3$)$_2$, —CN or —NO$_2$, especially, independently of one another, they are halogen, $C_1$–$C_2$-alkyl, halogen-$C_1$–$C_2$-alkyl, $C_1$–$C_2$-alkoxy or halogen-$C_1$–$C_2$-alkoxy;

particularly, independently of one another, they are fluorine, chlorine, methyl, trifluoromethyl, methoxy or trifluoromethoxy;

in particular, independently of one another, they are fluorine, trifluoromethyl or trifluoromethoxy;

most particularly wherein the two substituents are the same, m and n are 1, and $R_1$ and $R_2$ are in para-position;

b) $R_3$ is hydrogen, OH, halogen or $C_1$–$C_6$-alkoxy;

in particular hydrogen, OH, fluorine or methoxy;

especially hydrogen or OH, preferably OH;

c) $R_4$ is $C_1$–$C_2$-Alkyl, halogen-$C_1$–$C_2$-alkyl, $C_3$–$C_6$-cycloalkyl, $C_3$–$C_6$-cycloalkoxy, halogen-$C_1$–$C_2$-alkoxy, $C_2$–$C_4$-alkenyl, $C_2$–$C_4$-alkinyl, $C_1$–$C_2$-alkoxy, halogen-$C_1$–$C_2$-alkoxy, —C(=O)—$C_3$–$C_6$-alkyl , —C(=O)-halogen-$C_1$–$C_2$-alkyl, —C(=O)—OC$_1$–$C_2$-alkyl, —C(=O)—O-halogen-$C_1$–$C_2$alkyl, —NH—C(=O)—O—$C_1$–$C_2$-alkyl, —NH—C(=O)—O-halogen-$C_1$–$C_2$-alkyl, —C(=O)N(R$_5$)$_2$, —CN, —S(=O)$_2$N(R$_5$)$_2$, —S(=O)$_p$—$C_1$–$C_2$alkyl, —S(=O)$_p$-halogen-$C_1$–$C_2$-alkyl, —O—S(=O)$_p$—$C_1$–$C_6$-alkyl, —O—S(=O)$_p$-halogen-$C_1$–$C_6$-alkyl;

benzyl, phenoxy, benzyloxy; or phenyl, benzyl, phenoxy or benzyloxy which, independently of each other, is mono- to penta-substituted by substituents selected from the group consisting of halogen, cyano, $C_1$–$C_6$-alkyl, $C_3$–$C_8$-cycloalkyl, $C_3$–$C_8$-cycloalkyl-$C_1$–$C_6$-alkyl, halogen-$C_1$–$C_6$-alkyl, $C_1$–$C_6$-alkoxy, $C_3$–$C_8$-cycloalkoxy, $C_3$–$C_8$-cycloalkoxy-$C_1$–$C_6$-alkyl, $C_3$–$C_8$-cycloalkyl-$C_1$–$C_6$-alkoxy, halogen-$C_1$–$C_6$-alkoxy, $C_2$–$C_4$-alkenyl, $C_2$–$C_4$-alkinyl, $C_2$–$C_6$-alkenyloxy, $C_2$–$C_6$-alkinyloxy, —NH—C(=O)—O—$C_1$–$C_6$-alkyl, —NH—C(=O)—O-halogen-$C_1$–$C_6$-alkyl, —C(R$_7$)=N—W—R$_8$, phenyl, benzyl, phenoxy, benzyloxy, heterocyclyl and heterocyclyloxy, wherein the heterocyclyl and heterocyclyloxy radicals are optionally substituted by $C_1$–$C_4$-alkyl; especially wherein $R_4$ is phenyl which, independently, is mono- or disubstituted, especially mono-substituted, especially in para-position, by substituents selected from the group consisting of fluorine, $C_1$–$C_6$-alkoxy, $C_3$–$C_8$-cycloalkoxy, $C_3$–$C_8$-cycloalkoxy-$C_1$–$C_6$-alkyl, $C_3$–$C_8$- cycloalkyl-$C_1$–$C_6$-alkoxy, halogen-$C_1$–$C_6$-alkoxy, $C_2$–$C_6$-alkenyloxy, $C_2$–$C_6$-alkinyloxy, —NH—C(=O)—O—$C_1$–$C_4$-alkyl, —C($R_7$)=N—W—$R_8$, pyridyloxy, pyridazinyloxy, and tetrazolyl, wherein the tetrazolyl radicals are substituted by $C_1$–$C_4$-alkyl, halogen-$C_1$–$C_4$-alkyl, or $C_3$-alkenyl;

d) $R_5$ is $C_1$–$C_2$-alkyl; especially methyl;
e) $R_6$ is hydrogen or $C_1$–$C_3$-alkyl; especially hydrogen;
f) m is 1, 2, or 3; especially 1 or 2; in particular 1;
g) n is 1, 2, or 3; especially 1 or 2; in particular 1;
h) p is 1 or 2; especially 2;
i) q is 1.
k) $R_7$ is halogen, $C_1$–$C_6$-alkyl, $C_3$–$C_8$-cycloalkyl, $C_3$–$C_8$-cycloalkyl-$C_1$–$C_6$-alkyl, halogen-$C_1$–$C_6$-alkyl, $C_1$–$C_6$-alkoxy, $C_3$–$C_8$-cycloalkoxy, $C_3$–$C_8$-cycloalkoxy-$C_1$–$C_6$-alkyl, halogen-$C_1$–$C_6$-alkoxy —NH($C_1$–$C_6$-alkyl) or —N($C_1$–$C_6$-alkyl)$_2$;
l) $R_8$ is hydrogen, $C_1$–$C_2$-alkyl, $C_3$–$C_8$-cycloalkyl, $C_1$–$C_2$-halogenalkyl or —C(=O)—$C_1$–$C_6$-alkyl.
m) W is O or NH; especially O;

Particularly preferred in terms of the invention are the compounds of formula (I) listed in Table 2.

Therefore, a further object of the invention is a process, which is known to a person skilled in the art, for the production of the novel compounds of formula (I), or a salt thereof, characterised in that 1) in order to prepare a compound of formula (I), wherein q is 0, a compound of formula

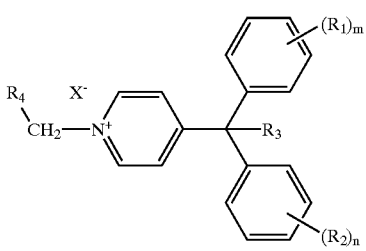
(II)

wherein $(R_1)_m$, $(R_2)_n$, $R_4$ are defined as given above for formula (I) and X is an ion of opposite charge, such as halogen, sulphate or phosphate, and which is known or may be prepared by known processes, is treated with a reduction agent, for example $NaBH_4$, where appropriate in a solvent that is inert under the chosen reaction conditions, and 2) the compound of formula (I) thus obtained, wherein q is 0, is optionally reacted with an oxidation agent, especially $H_2O_2$.

The compounds of formula (II) may be obtained whereby 3) where $(R_1)_m$, and $(R_2)_n$ are the same, a compound of formula

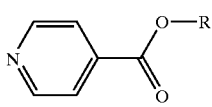
(III)

wherein R is $C_1$–$C_{12}$-alkyl, is reacted with two mols of a compound of formula

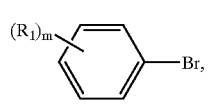
(IV)

which is known or may be prepared by known processes, and wherein $(R_1)_m$ is defined as given above for formula (I), in the presence of magnesium or n-butyllithium; and 4) the compound of formula

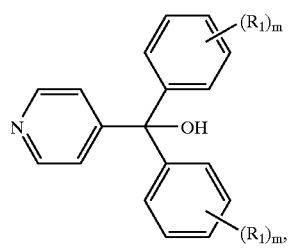
(V)

thus obtained, wherein $R_1$ and m are defined as given for formula (I), is reacted with a compound of formula

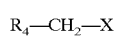
$R_4$—$CH_2$—X (VI), wherein $R_4$ is defined as given above for formula (I) and X is a leaving group, preferably chlorine or bromine.

A further object of the invention is a process for the production of compounds of formula (I), or a salt thereof, characterised in that 5) in order to prepare a compound of formula (I), wherein $(R_1)_m$ and $(R_2)_n$ are the same or different and $R_3$ is OH, a compound of formula (IV) is reacted with isonicotinonitrile in the presence of magnesium or n-butyllithium, and the compound of formula

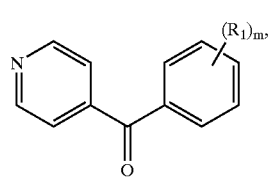
(VII)

obtained after acidic hydrolysis, wherein $(R_1)_m$ is defined as given above for formula (I), is reacted with a compound of formula

(VIII)

which is known or may be prepared by known processes, and wherein $(R_2)_n$ is defined as given above for formula (I), in the presence of magnesium or n-butyllithium; and the compound of formula

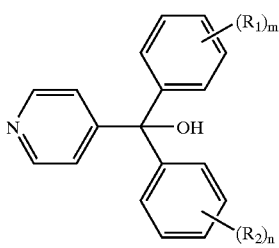

(IX)

thus obtained, wherein $(R_1)_m$ and $(R_2)_n$ are defined as given above for formula (I), is further reacted analogously to process steps 4), 1) and optionally 2), to form a compound of formula (I).

6) in order to produce a compound of formula (I), wherein $R_3$ is hydrogen, a compound of formula (IX) is reacted with a reduction agent, for example triethylsilane, in the presence of trifluoroacetic acid or trifluoromethanesulphonic acid, to form a compound of formula

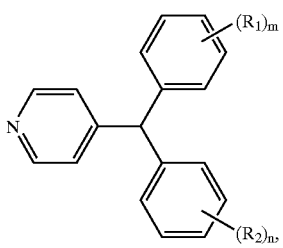

(X)

wherein $(R_1)_m$ and $(R_2)_n$ are defined as given above for formula (I), and this compound of formula (X) is further reacted analogously to process steps 4), 1) and optionally 2).

7) in order to produce a compound of formula (I), wherein $R_3$ is alkoxy, a compound of formula (IX) is reacted with an alkyl halide in the presence of a strong base, such as sodium hydride, to form a compound of formula

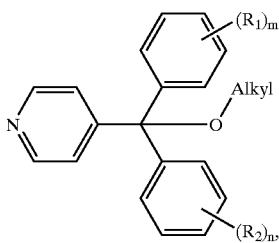

(XI)

wherein $(R_1)_m$ and $(R_2)_n$ are defined as given above for formula (I), and this compound of formula (XI) is further reacted analogously to process steps 4), 1) and optionally 2) to form a compound of formula (I).
and/or, if so desired, a compound of formula (I) obtainable according to the method or by other means, present in free form or in the form of a salt, is converted into a different compound of formula (I), a mixture of isomers obtainable according to the method is separated and the desired isomer is isolated and/or a free compound of formula (I) obtainable according to the method or by other means is converted into a salt, or a salt of a compound of formula (I) obtainable according to the method or by other means is converted into the free compound of formula (I) or into a different salt.

The starting materials of formulae (III), (IV), (VI) and (VIII) listed hereinbefore and hereinafter, which are used to produce the compounds of formula (I), in free form or in salt form, are known or may be produced by methods known per se. The compounds of formula (II), (V), (IX), (X) and (XI) are partly known. If they are new, they therefore similarly form an object of the invention.

The reactions described hereinbefore and hereinafter are carried out in a known manner, e.g. in the absence or, where appropriate, in the presence of a suitable solvent or diluent or a mixture thereof, proceeding as required under conditions of cooling, of ambient temperature, or of heating, e.g. in a temperature range of about −80° C. to the boiling temperature of the reaction medium, preferably about −20° C. to about +150° C., and where appropriate in a closed vessel, under pressure, in an inert gas atmosphere, and/or under non-aqueous conditions. Especially advantageous reaction conditions are described in the Examples.

A leaving group is understood to be hereinbefore and hereinafter all the removable groups that are usual in chemical reactions and are known to the person skilled in the art; in particular halogens such as fluorine, chlorine, bromine, iodine, —O—C(=O)—A, —O—P(=O)(W)$_2$, —O—Si($C_1$-$C_8$-alkyl)$_3$, —O—($C_1$-$C_8$-alkyl), —O-aryl, —O—S(=O)$_2$W, —S—P(=O)(W)$_2$, —S—P(=S)(W)$_2$, —S—S—($C_1$-$C_8$-alkyl), —S—S-aryl, —S—($C_1$-$C_8$-alkyl), —S-aryl, —S(=O)W, or —S(=O)$_2$W, wherein W is optionally substituted $C_1$-$C_8$-alkyl, $C_2$-$C_8$-alkenyl, $C_2$-$C_8$-alkinyl, optionally substituted aryl, optionally substituted benzyl, $C_1$-$C_8$-alkoxy or di-($C_1$-$C_8$-alkyl)amine, in which the alkyl groups are independent of one another; $NO_3$, $NO_2$ or sulphate, sulphite, phosphate, phosphite, carboxylate, imino ester, $N_2$ or carbamate. Chlorine and bromine are especially preferred as the leaving group, particularly chlorine.

The oxidation agents employed are for example inorganic peroxides, such as sodium perborate, potassium permanganate or hydrogen peroxide; or mCPBA or organic per acids, such as perbenzoic acid or peracetic acid, or mixtures of organic acids and hydrogen peroxide, such as acetic acid/hydrogen peroxide.

The reaction of process 1) preferably takes place in alcohols, such as methanol or ethanol, in a temperature range of 0° C. to +50° C., preferably at room temperature. The preferred reduction agent is sodium borohydride.

In process variant 2), the solvents used are preferably alcohols, such as methanol or ethanol. It is preferable to operate at room temperature; suitable oxidation agents are especially $H_2O_2$ or per acids, in particular $H_2O_2$.

In process variants 3) and 5), the solvent used is preferably a dialkylether or tetrahydrofuran; the process is carried out in a temperature range of −70° C. to room temperature, and the metallising agent used is magnesium or n-butyllithium.

In process variant 4), inert solvents, such as benzene, toluene, xylenes, acetonitrile, propionitrile, ethyl acetate, propyl acetate, butyl acetate, acetone, diethyl ketone, methyl ethyl ketone or methyl isobutyl ketone, are used. The temperature range is from room temperature to reflux temperature of the corresponding solvent, with reflux temperature being preferred.

In process variant 6), the reduction agent employed is preferably triethylsilane in the presence of an acid, such as trifluoroacetic acid or trifluoromethanesulphonic acid.

In process variant 7), dimethylformamide or tetrahydrofuran is suitable as the solvent, preferably dimethylformamide; the preferred base is sodium hydride.

Compounds of formula (I) obtainable according to the method or by other means may be converted in a manner known per se into other compounds of formula (I), by replacing one or more substituents of the starting compound of formula (I) in conventional manner with (an)other substituent(s) according to the invention.

Depending on the choice of appropriate reaction conditions and starting materials, it is possible to replace only one substituent with another substituent according to the invention in one reaction step, or several substituents may be replaced with other substituents according to the invention in the same reaction step.

Salts of compounds of formula (I) may be prepared in a known manner. For example, it is possible to obtain salts of compounds of formula (I) with bases, by treating the free compounds with an appropriate base or with an appropriate ion exchange reagent.

Salts of compounds of formula (I) may be converted in conventional manner into the free compounds of formula (I), e.g. by treatment with a suitable acid or with a suitable ion exchange reagent.

Salts of compounds of formula (I) may be transformed in known manner into other salts of a compound of formula (I).

The compounds of formula (I) in free form or in salt form may exist in the form of one of the possible isomers or as a mixture thereof, e.g. depending on the number, the absolute and relative configuration of asymmetric carbon atoms appearing in the molecule and/or depending on the configuration of non-aromatic double bonds appearing in the molecule, as pure isomers such as antipodes and/or diastereoisomers, or as isomer mixtures such as enantiomer mixtures, e.g. racemates, diastereoisomer mixtures or racemate mixtures. The invention relates both to the pure isomers and to all the possible mixtures of isomers, and hereinbefore and hereinafter is to be understood as such accordingly, even if the stereo-chemical details are not specifically mentioned in each case.

Depending on the choice of starting materials and methods, diastereoisomer mixtures, racemate mixtures and mixtures of double bond isomers of compounds of formula (I) in free form or in salt form, which are obtainable by the process or in another way, may be separated in known manner, on the basis of the physical-chemical differences in their components, into the pure diastereoisomers or racemates, for example by fractional crystallisation, distillation and/or chromatography.

Enantiomer mixtures that are obtainable correspondingly, such as racemates, may be broken down by known methods into the optical antipodes, for example by recrystallisation from an optically active solvent, by chromatography on chiral adsorbents, e.g. high pressure liquid chromatography on acetyl cellulose, with the assistance of suitable microorganisms, by cleavage with specific, immobilised enzymes, through the formation of inclusion compounds, e.g. using chiral crown ethers, whereby only one enantiomer is complexed, or by converting into diastereoisomeric salts and separating the diastereoisomer mixture obtained in this way, e.g. on the basis of their different solubilities, by fractional crystallisation, into the diastereoisomers, from which the desired enantiomer can be released upon the action of suitable agents.

According to the invention, apart from isolation of corresponding isomer mixtures, generally known methods of diastereoselective or enantioselective synthesis can also be applied to obtain pure diastereoisomers or enantiomers, e.g. by carrying out the method of the invention using educts with correspondingly suitable stereochemistry.

It is advantageous to isolate or synthesise the biologically more active isomer, e.g. enantiomer or diastereoisomer, or isomer mixture, e.g. enantiomer mixture or diastereoisomer mixture, provided that the individual components have differing biological efficacy.

Compounds of formula (I) in free form or in salt form can also be obtained in the form of their hydrates and/or also can include other solvents, used for example where necessary for the crystallisation of compounds present in solid form.

The invention relates to all those forms of the method, according to which one starts from a compound obtainable as a primary material or an intermediate at any stage of the method and carries out all or some of the missing steps, or uses, or—especially under the reaction conditions—produces a starting material in the form of a derivative or a salt and/or its racemate or enantiomer.

In the method of the present invention, the starting materials and intermediates used, each in free form or in salt form, are preferably those that lead to the compounds of formula (I) or salts thereof described at the beginning as being especially useful.

The invention relates especially to the method of preparation described in Example P1.

The compounds of formula (I) according to the invention are active substances of preventive and/or curative merit for use in pest control and offer a very favourable spectrum of biocidal activity with favourable tolerability in warm-blooded animals, fish, and plants even at low concentrations. The active ingredients according to the invention are active against all or individual development stages of animal pests showing normal sensitivity, as well as those showing resistance, such as insects or members of the order Acarina. The insecticidal or acaricidal effect of the active substances of the invention can manifest itself directly, i.e. killing the pests either immediately or after some time has elapsed, for example when moulting occurs, or indirectly, e.g. reducing the number of eggs laid and/or the hatching rate, good efficacy corresponding to a pesticidal rate (mortality) of at least 50 to 60%.

The said animal pests include, for example, those which are mentioned in the European Patent application EP-A-736'252. The pests mentioned therein are thus included by reference in the object of the present invention. The active ingredients according to the invention are especially suitable for controlling *Boophilus microplus, Nilaparvata lugens* and *Tetranychus urticae*, preferably for controlling these pests in vegetable, fruit and rice crops.

Pests of said type which occur on plants, especially on crops and ornamentals in agriculture, horticulture and forestry, or on parts of such plants, such as fruits, blooms, leaves, stems, tubers or roots, can be controlled, i.e. kept in check or eradicated, using the active ingredients of the invention, this protection remaining for parts of some plants whose growth does not occur until later.

Target crops include especially cereals, such as wheat, barley, rye, oats, rice, corn or sorghum; beet, such as sugar beet or fodder beet; fruit, e.g. pomes, drupes and soft fruit, such as apples, pears, plums, peaches, almonds, cherries or berries, e.g. strawberries, raspberries or blackberries; leguminous plants, such as beans, lentils, peas or soybean; oleaginous fruits, such as rape, mustard, poppy, olives, sunflowers, coconut, castor oil plants, cocoa beans or groundnuts; cucumber plants, such as squashes, cucumbers or melons; fibrous plants, such as cotton, flax, hemp or jute; citrus fruits, such as oranges, lemons, grapefruit or mandarins; vegetables, such as spinach, lettuce, asparagus, cabbages, carrots, onions, tomatoes, potatoes or paprika; lauraceae, such as avocado, cinnamon or camphor; and tobacco, nuts, coffee, aubergines, sugar cane, tea, pepper, vines, hops, banana plants, natural rubber plants and ornamentals.

Other indication areas for the active ingredients of the invention are the protection of stored products and stores and of material and, in the hygiene sector, especially the protection of domestic animals and livestock against pests of said type.

The invention therefore relates also to pesticides, such as emulsifiable concentrates, suspension concentrates, ready-to-spray or ready-to-dilute solutions, coatable pastes, dilute emulsions, spray powders, soluble powders, dispersible powders, wettable powders, dusts, granulates or encapsulations in polymeric substances (chosen in accordance with the intended objectives and prevailing circumstances), comprising at least one active ingredient of the invention.

The active ingredient is used in these compositions in pure form and a solid active ingredient e.g. in a specific particle size, or preferably together with at least one of the adjuvants conventionally employed in the art of formulation, such as extenders, e.g. solvents or solid carriers, or surface-active compounds (surfactants).

The adjuvants which can be used for formulation are, for example, solid carriers, solvents, stabilizers, "slow-release" agents, dyes, and where appropriate surfactants. Carriers and adjuvants can be any substance conventionally used in crop protection agents, especially agents for slug and snail control. Adjuvants such as solvents, solid carriers, surface-active agents, non-ionic surfactants, cationic surfactants, anionic surfactants, and other adjuvants in the compositions of the invention can, for example, be the same as those described in EP-A-736'252, and are included by reference in the object of the present invention.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable concentrates:
  Active ingredient: 1 to 95%, preferably 5 to 20%
  Surfactant: 1 to 30%, preferably 10 to 20%
  Solvent: 5 to 98%, preferably 70 to 85%
Dusts:
  Active ingredient: 0.1 to 10%, preferably 0.1 to 1%
  Solid carrier 99.9 to 90%, preferably 99.9 to 99%
Suspension concentrates:
  Active ingredient: 5 to 75%, preferably 10 to 50%
  water: 94 to 24%, preferably 88 to 30%
  Surfactant: 1 to 40%, preferably 2 to 30%
Wettable powders:
  Active ingredient: 0.5 to 90%, preferably 1 to 80%
  Surfactant: 0.5 to 20%, preferably 1 to 15%
  Solid carrier 5 to 99%, preferably 15 to 98%
Granulates:
  Active ingredient: 0.5 to 30%, preferably 3 to 15%
  Solid carrier 99.5 to 70%, preferably 97 to 85%

The activity of the compositions of the invention can be substantially broadened and adapted to prevailing circumstances by adding other insecticidal substances. Additional active ingredients are, for example, substances from the following classes: organic phosphorus compounds, nitrophenols and their derivatives, formamidines, acylureas, carbamates, pyrethroids, nitroenamines and their derivatives, pyrroles, thioureas and their derivatives, chlorinated hydrocarbons and *Bacillus thuringiensis* preparations. The compositions of the invention can also contain further solid or liquid adjuvants, such as stabilisers, e.g. vegetable oils, epoxidised where appropriate (e.g. epoxidised coconut oil, rapeseed oil or soya oil), antifoaming agents, e.g. silicone oil, preservatives, viscosity modulators, binders and/or tackifiers, as well as fertilisers or other active ingredients to achieve specific effects, e.g. acaricides, bactericides, fungicides, nematocides, molluscicides or selective herbicides.

The compositions of the invention are prepared in a known manner, in the absence of adjuvants, for example, by grinding, sieving, and/or compressing a solid active ingredient or active ingredient mixture, e.g. to a specific particle size, and in the presence of at least one adjuvant, for example, by intimately mixing and/or grinding the active ingredient or the mixture of active ingredients with the adjuvant(s). These methods for preparing compositions of the invention and the use of compounds of the formula (I) for preparing these compositions likewise form an object of the invention.

The methods of application for the compositions, i.e. the methods of controlling pests of said type, such as spraying, atomising, dusting, coating, dressing, scattering or pouring, which are chosen in accordance with the intended objectives and prevailing circumstances, and the use of the compositions for controlling pests of said type are further objects of the invention. Typical concentrations of active ingredient are between 0.1 and 1000 ppm, preferably between 0.1 and 500 ppm. The rates of application are generally 1 to 2000 g of active ingredient per hectare, especially 10 to 1000 g/ha, and preferably 20 to 600 g/ha.

A preferred method of application for crop protection is to apply the active ingredient to the foliage of the plants (leaf application), the number of applications and the rate of application depending on the intensity of infestation by the pest in question. However, the active ingredients can also penetrate the plant through the roots (systemic action) by impregnating the locus of the plant with a liquid composition, or by applying the active ingredient in solid form to the locus of the plants, e.g. the soil, for example in granular form (soil application). With paddy rice cultures, granules may be metered into the flooded paddy field.

The compositions of the invention are also suitable for protecting plant propagation material, including genetically modified propagation material, e.g. seeds, such as fruits, tubers or grains, or plant seedlings, from animal pests. The propagation material can be treated with the composition before the start of cultivation, seeds for example being dressed before they are sown. The active ingredients of the invention can also be applied to seeds (coating) by either soaking the seeds in a liquid composition or coating them with a solid composition. The composition can also be applied when the propagation material is introduced to the place of cultivation, e.g. when the seeds are sown in the seed furrow. The treatment procedures for plant propagation material and the propagation material thus treated are further objects of the invention.

The invention is illustrated by the following examples. They do not impose any limitation on the invention. The temperatures are given in degrees Celsius, and the proportions of solvents in the mixture are given as parts by volume.

PREPARATION EXAMPLES

Preparation Example P1

Preparation of the Compound of Formula

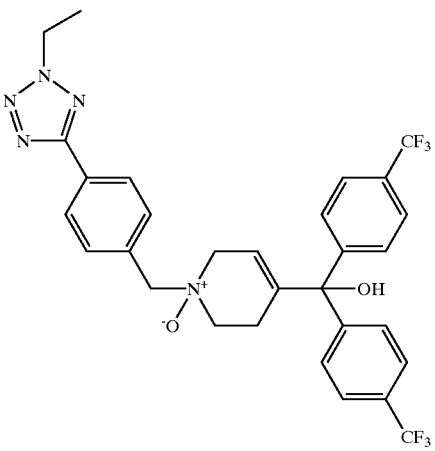

a) Preparation of the Compound of Formula

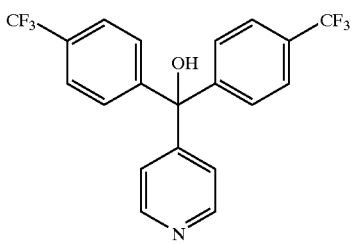

(A)

3.4. g of magnesium are coated with 20 ml of diethylether and then 30.0 g of 4-bromobenzotrifluoride in 80 ml of diethylether are slowly added dropwise whilst stirring. After stirring for 1 hour, 6.1 ml of isonicotinic acid ethyl ester in 40 ml of diethylether are slowly added dropwise, and stirring continues for a further 5 hours. Then, the mixture is carefully hydrolysed with diluted acetic acid, washed twice with water and once with sodium chloride solution, the organic phase is dried over sodium sulphate and concentrated under vacuum. The residue is chromatographed on silica gel with hexane/ethyl acetate (2:1). A yellow oil is obtained, which crystallises from diethylether/hexane. beige crystals, m.p. 161–163° C.

b) Preparation of the Compound of Formula

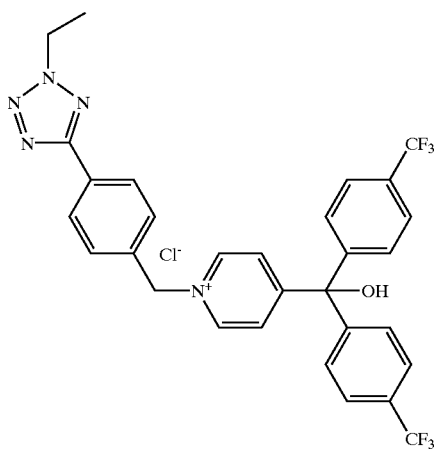

(B)

2.0 g of the above compound (A) and 1.4 g of the compound of formula

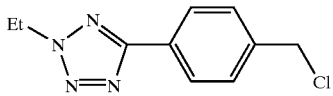

(C)

are heated for 72 hours under reflux in 50 ml of toluene. After cooling the reaction mixture and adding diethylether dropwise, compound (C) crystallises in the form of colourless crystals, m.p. 233–242° C.

c) Preparation of the Compound of Formula

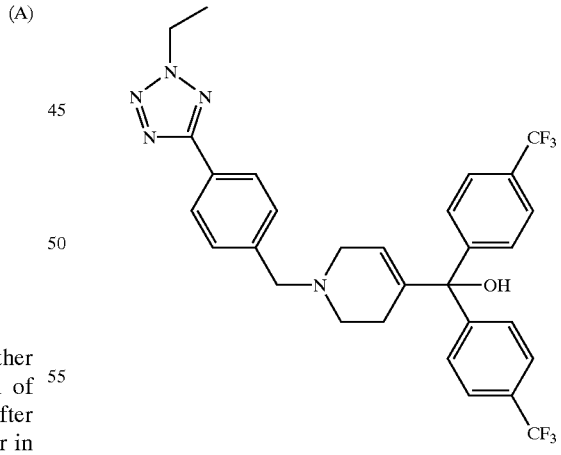

(D)

1.2 g of compound (B) in 20 ml of methanol are mixed in portions with 0.14 g of sodium borohydride and stirred for 1 hour. After adding 1 ml of acetone, the reaction mixture is mixed with ethyl acetate and washed twice with water and once with sodium chloride solution, the organic phase is dried over sodium sulphate and concentrated under vacuum. (D) is obtained as a colourless foam.

d) Preparation of the Title Compound 0.84 g of compound (D) in 25 ml of methanol are stirred for 48 hours at room temperature together with 2.8 ml of 30% hydrogen peroxide. The reaction mixture is mixed with ethyl acetate and washed twice with water and once with sodium chloride solution, the organic phase is dried over sodium sulphate and concentrated under vacuum. The compound crystallises from dichloromethane/hexane in the form of colourless crystals, m.p. 156–167° C.

Example P2

The remaining compounds of Tables 1 and 2 may be produced analogously to the manner described above. In the tables, m.p. indicates the meting point in ° C., Me is methyl, Et is ethyl, i-prop is isopropyl, i-but is isobutyl and c-prop is cyclopropyl.

TABLE 1

Compounds of formula (IIa)

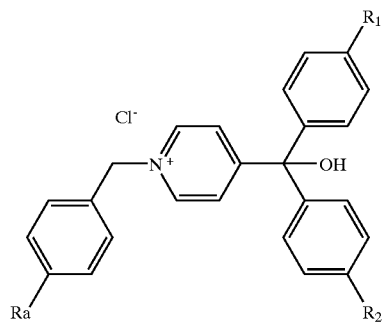

| Ex. No. | $R_1$ | $R_2$ | $R_a$ | melting point |
|---|---|---|---|---|
| 1.1 | $OCF_3$ | $OCF_3$ | n-propoxy | 147–150 |
| 1.2 | $OCF_3$ | $OCF_3$ | OMe | 108–114 |
| 1.3 | $OCF_3$ | $OCF_3$ | benzyloxy | 149–151 |
| 1.4 | $OCF_3$ | $OCF_3$ | cyclopentyloxy | 137–145 |
| 1.5 | $OCF_3$ | $CF_3$ | i-propyloxy | 76–84 |
| 1.6 | $OCF_3$ | OMe | i-propyloxy | solid |
| 1.7 | $OCF_3$ | F | i-propyloxy | 58–63° C. |
| 1.8 | $CF_3$ | OMe | —O—$CH_2$-c-prop. | 111–118 |
| 1.9 | $OCF_3$ | $CF_3$ | 2-pyridyloxy | 83–90 |
| 1.10 | $OCF_3$ | $OCF_3$ | NHCOOEt | 135–143 |
| 1.11 | $CF_3$ | $CF_3$ | NHCOOEt | 238–240 |
| 1.12 | $CF_3$ | F | NHCOOEt | solid |
| 1.13 | $OCF_3$ | OMe | NHCOOEt | 179–184 |
| 1.14 | $OCF_3$ | $OCF_3$ | NHCOO-i-prop. | 130–133 |
| 1.15 | $CF_3$ | $CF_3$ | NHCOO-i-prop | 239–241 |
| 1.16 | $CF_3$ | $CF_3$ | tetrazolyl-Et | 233–242 |
| 1.17 | Cl | Cl | NHCOO-i-butyl | 150–153 |
| 1.18 | $CF_3$ | $CF_3$ | NHCOO-i-butyl | 145–147 |
| 1.19 | $OCF_3$ | $OCF_3$ | tetrazolyl-Et | 206–208 |
| 1.20 | $OCF_3$ | $CF_3$ | tetrazolyl-Et | 203–205 |
| 1.21 | $CF_3$ | $CF_3$ | tetrazolyl-i-Prop. | 229–232 |
| 1.22 | $CF_3$ | $CF_3$ | tetrazolyl-Me | 260–262 |
| 1.23 | $CF_3$ | $CF_3$ | 3-methoxy-6-chloropyridazinyl | 247–249 |
| 1.24 | t-but | t-but | NHCOO-i-prop | 190–197 |
| 1.25 | $CF_3$ | $CF_3$ | tetrazolyl-$CH_2$—CH=$CH_2$ | 135–140 |
| 1.26 | $CF_3$ | $CF_3$ | tetrazolyl-$CH_2CH_2F$ | 224–227 |
| 1.27 | $OCF_3$ | $CF_3$ | tetrazolyl-$CH_2CH_2F$ | 193–197 |
| 1.28 | $OCF_3$ | $OCF_3$ | tetrazolyl-$CH_2CH_2F$ | 188–192 |
| 1.29 | $CF_3$ | $CF_3$ | —$C_6H_5$ | 160–165 |
| 1.30 | $CF_3$ | $CF_3$ | 6-methoxy-2-fluoropyridyl | 210–212 |
| 1.31 | $OCF_3$ | $OCF_3$ | 6-methoxy-2-fluoropyridyl | 116–120 |
| 1.32 | $CF_3$ | $CF_3$ | 3-methoxy-6-methoxypyridazinyl | 195–200 |

TABLE 2

Compounds of formula (Ia)

| No. | $R_1$ | $R_2$ | Ra | $R_3$ | q | phys. data |
|---|---|---|---|---|---|---|
| 2.1 | $OCF_3$ | $OCF_3$ | n-propoxy | OH | 0 | resin |
| 2.2 | $OCF_3$ | $OCF_3$ | OEt | OH | 0 | resin |
| 2.3 | $OCF_3$ | $OCF_3$ | n-butoxy | OH | 0 | resin |
| 2.4 | $OCF_3$ | $OCF_3$ | OMe | OH | 0 | resin |
| 2.5 | $OCF_3$ | $OCF_3$ | n-propoxy | OH | 1 | m.p. 175 |
| 2.6 | $OCF_3$ | $OCF_3$ | —O—$CH_2$-c-Prop. | OH | 0 | foam |
| 2.7 | $OCF_3$ | $OCF_3$ | allyloxy | OH | 0 | resin |
| 2.8 | $OCF_3$ | $OCF_3$ | i-butyloxy | OH | 0 | foam |
| 2.9 | $OCF_3$ | $OCF_3$ | propargyloxy | OH | 0 | oil |
| 2.10 | $OCF_3$ | $OCF_3$ | benzyloxy | OH | 0 | resin |
| 2.11 | $OCF_3$ | $OCF_3$ | s-butyloxy | OH | 0 | resin |
| 2.12 | $OCF_3$ | $OCF_3$ | i-propyloxy | OH | 0 | resin |
| 2.13 | $OCF_3$ | $OCF_3$ | F | OH | 0 | resin |
| 2.14 | $CF_3$ | $CF_3$ | n-propoxy | OH | 0 | foam |
| 2.15 | F | OMe | n-propoxy | OH | 0 | resin |
| 2.16 | $OCF_3$ | $OCF_3$ | cyclopentyloxy | OH | 0 | foam |
| 2.17 | $OCF_3$ | $OCF_3$ | n-propoxy | OH | 0 | resin |
| 2.18 | $OCF_3$ | F | n-propoxy | OH | 0 | resin |
| 2.19 | $CF_3$ | OMe | n-propoxy | OH | 0 | resin |
| 2.20 | $OCF_3$ | OMe | OEt | OH | 0 | foam |
| 2.21 | $OCF_3$ | F | OEt | OH | 0 | foam |
| 2.22 | $OCF_3$ | F | n-butoxy | OH | 0 | resin |
| 2.23 | $CF_3$ | $CF_3$ | OEt | OH | 0 | foam |
| 2.24 | $CF_3$ | $CF_3$ | n-butoxy | OH | 0 | foam |
| 2.25 | $OCF_3$ | OMe | n-butoxy | OH | 0 | resin |
| 2.26 | $OCF_3$ | $CF_3$ | n-butoxy | OH | 0 | foam |
| 2.27 | $OCF_3$ | $CF_3$ | OEt | OH | 0 | foam |
| 2.28 | $CF_3$ | $OCF_3$ | —O—$CH_2$-c-prop. | OH | 0 | foam |
| 2.29 | $OCF_3$ | F | —O—$CH_2$-c-prop. | OH | 0 | foam |
| 2.30 | $OCF_3$ | $CF_3$ | —O—$CH_2$-c-prop. | OH | 0 | foam |
| 2.31 | $OCF_3$ | OMe | —O—$CH_2$-c-prop. | OH | 0 | foam |
| 2.32 | $OCF_3$ | OMe | allyloxy | OH | 0 | resin |
| 2.33 | $OCF_3$ | $CF_3$ | allyloxy | OH | 0 | oil |
| 2.34 | $OCF_3$ | F | i-propyloxy | OH | 0 | foam |
| 2.35 | $OCF_3$ | OMe | i-propyloxy | OH | 0 | foam |
| 2.36 | $OCF_3$ | $CF_3$ | i-propyloxy | OH | 0 | foam |
| 2.37 | $OCF_3$ | $CF_3$ | propargyloxy | OH | 0 | resin |
| 2.38 | $OCF_3$ | OMe | propargyloxy | OH | 0 | resin |
| 2.39 | $OCF_3$ | F | propargyloxy | OH | 0 | oil |
| 2.40 | $OCF_3$ | F | allyloxy | OH | 0 | resin |
| 2.41 | $CF_3$ | OMe | n-butoxy | OH | 0 | resin |
| 2.42 | $CF_3$ | OMe | OEt | OH | 0 | foam |
| 2.43 | $OCF_3$ | $OCF_3$ | F | OH | 1 | m.p. 97–100 |
| 2.44 | $CF_3$ | OMe | allyloxy | OH | 0 | resin |
| 2.45 | $CF_3$ | OMe | propargyloxy | OH | 0 | resin |
| 2.46 | $CF_3$ | OMe | —O—$CH_2$-c-prop. | OH | 0 | foam |
| 2.47 | $OCF_3$ | $OCF_3$ | propargyloxy | OH | 1 | m.p. 98–102 |
| 2.48 | $OCF_3$ | $CF_3$ | allyloxy | OH | 1 | m.p. 105–110 |
| 2.49 | $CF_3$ | $CF_3$ | n-propoxy | OH | 1 | m.p. 135–140 |
| 2.50 | $OCF_3$ | $CF_3$ | n-butoxy | OH | 1 | m.p. 124–127 |
| 2.51 | $CF_3$ | $CF_3$ | n-butoxy | OH | 1 | m.p. 167–172 |
| 2.52 | $CF_3$ | $CF_3$ | OEt | OH | 1 | m.p. 183–188 |
| 2.53 | $OCF_3$ | $CF_3$ | —O—$CH_2$-c-prop. | OH | 1 | m.p. 181–184 |
| 2.54 | $CF_3$ | $CF_3$ | —O—$CH_2$-c-prop. | OH | 1 | m.p. 189–191 |
| 2.55 | $OCF_3$ | $OCF_3$ | cyclopentyloxy | OH | 1 | foam |
| 2.56 | $CF_3$ | F | n-propoxy | OH | 0 | resin |
| 2.57 | $CF_3$ | F | n-butoxy | OH | 0 | resin |
| 2.58 | $CF_3$ | F | —O—$CH_2$-c-prop. | OH | 0 | resin |

TABLE 2-continued

Compounds of formula (Ia)

| No. | R₁ | R₂ | Ra | R₃ | q | phys. data |
|---|---|---|---|---|---|---|
| 2.59 | CF₃ | F | allyloxy | OH | 0 | resin |
| 2.60 | CF₃ | F | propargyloxy | OH | 0 | foam |
| 2.61 | CF₃ | F | propargyloxy | OH | 1 | foam |
| 2.62 | CF₃ | F | n-propoxy | OH | 1 | foam |
| 2.63 | CF₃ | F | —O—CH₂-c-prop. | OH | 1 | foam |
| 2.64 | OCF₃ | F | —O—CH₂-c-prop. | OH | 1 | m.p. 174–178 |
| 2.65 | OCF₃ | OCF₃ | 2-pyridyloxy | OH | 0 | foam |
| 2.66 | CF₃ | OMe | 2-pyridyloxy | OH | 0 | foam |
| 2.67 | OCF₃ | CF₃ | 2-pyridyloxy | OH | 0 | foam |
| 2.68 | OCF₃ | F | 2-pyridyloxy | OH | 0 | foam |
| 2.69 | OCF₃ | OCF₃ | NHCOOMe | OH | 0 | foam |
| 2.70 | OCF₃ | CF₃ | NHCOOMe | OH | 0 | foam |
| 2.71 | OCF₃ | OMe | 2-pyridyloxy | OH | 0 | foam |
| 2.72 | CF₃ | F | 2-pyridyloxy | OH | 0 | foam |
| 2.73 | CF₃ | CF₃ | 2-pyridyloxy | OH | 0 | foam |
| 2.74 | CF₃ | CF₃ | NHCOOMe | OH | 0 | foam |
| 2.75 | CF₃ | F | NHCOOMe | OH | 0 | foam |
| 2.76 | OCF₃ | OMe | NHCOOMe | OH | 0 | foam |
| 2.77 | OCF₃ | CF₃ | NHCOOMe | OH | 1 | m.p. 159–161 |
| 2.78 | OCF₃ | OCF₃ | NHCOOMe | OH | 1 | m.p. 159–161 |
| 2.79 | OCF₃ | OCF₃ | NHCOOEt | OH | 0 | foam |
| 2.80 | OCF₃ | OMe | NHCOOEt | OH | 0 | foam |
| 2.81 | OCF₃ | CF₃ | NHCOOEt | OH | 0 | foam |
| 2.82 | CF₃ | CF₃ | NHCOOEt | OH | 0 | foam |
| 2.83 | CF₃ | F | NHCOOEt | OH | 0 | foam |
| 2.84 | OCF₃ | OCF₃ | NHCOOEt | OH | 1 | m.p. 148–151 |
| 2.85 | OCF₃ | CF₃ | NHCOOEt | OH | 1 | m.p. 130–134 |
| 2.86 | CF₃ | CF₃ | NHCOOEt | OH | 1 | m.p. 154–157 |
| 2.87 | CF₃ | F | NHCOOEt | OH | 1 | m.p. 157–160 |
| 2.88 | OCF₃ | OCF₃ | NHCOOMe | H | 0 | foam |
| 2.89 | OCF₃ | OCF₃ | NHCOOMe | H | 1 | m.p. 147–150 |
| 2.90 | OCF₃ | OCF₃ | NHCOOEt | OMe | 0 | resin |
| 2.91 | OCF₃ | OCF₃ | NHCOOEt | OMe | 1 | m.p. 113–117 |
| 2.92 | OCF₃ | OCF₃ | NHCOOEt | H | 0 | foam |
| 2.93 | OCF₃ | OCF₃ | NHCOOEt | H | 1 | m.p. 135–139 |
| 2.94 | CF₃ | CF₃ | NHCOOMe | OH | 1 | m.p. 163–167 |
| 2.95 | CF₃ | CF₃ | NHCOO-i-prop. | OH | 0 | foam |
| 2.96 | OCF₃ | OCF₃ | NHCOO-i-prop. | OH | 0 | foam |
| 2.97 | CF₃ | CF₃ | 5-methyl-2-ethyl-tetrazol-yl | OH | 0 | foam |
| 2.98 | CF₃ | CF₃ | 5-methyl-2-ethyl-tetrazol-yl | OH | 1 | m.p. 156–167 |
| 2.99 | CF₃ | CF₃ | NHCOO-i-prop. | OH | 1 | m.p. 183–186 |
| 2.100 | OCF₃ | OCF₃ | NHCOO-i-prop. | OH | 1 | m.p. 181–184 |
| 2.101 | CF₃ | CF₃ | NHCOO-i-but. | OH | 0 | foam |
| 2.102 | Cl | Cl | NHCOO-i-but. | OH | 0 | foam |
| 2.103 | OCF₃ | CF₃ | 5-methyl-2-ethyl-tetrazol-yl | OH | 0 | foam |

TABLE 2-continued

Compounds of formula (Ia)

| No. | R₁ | R₂ | Ra | R₃ | q | phys. data |
|---|---|---|---|---|---|---|
| 2.104 | OCF₃ | OCF₃ | tetrazole-Et | OH | 0 | foam |
| 2.105 | OCF₃ | OCF₃ | tetrazole-i-Prop. | OH | 0 | foam |
| 2.106 | OCF₃ | OCF₃ | tetrazole-Et | OH | 1 | m.p. 173–175 |
| 2.107 | OCF₃ | CF₃ | tetrazole-Et | OH | 1 | m.p. 70–75° C. |
| 2.108 | Cl | Cl | NHCOO-i-but. | OH | 1 | m.p. 177–179 |
| 2.109 | CF₃ | CF₃ | NHCOO-i-but. | OH | 1 | m.p. 180–183 |
| 2.110 | OCF₃ | OCF₃ | tetrazole-i-Prop. | OH | 1 | m.p. 136–139 |
| 2.111 | CF₃ | CF₃ | tetrazole-i-Prop. | OH | 0 | foam |
| 2.112 | CF₃ | CF₃ | tetrazole-Me | OH | 0 | foam |
| 2.113 | OCF₃ | OCF₃ | NHCOO-i-but. | OH | 1 | m.p. 179–181 |
| 2.114 | CF₃ | CF₃ | tetrazole-i-Prop. | OH | 1 | m.p. 148–151 |
| 2.115 | CF₃ | CF₃ | tetrazole-Me | OH | 1 | m.p. 165–167 |
| 2.116 | OCF₃ | OCF₃ | tetrazole-Me | OH | 0 | foam |

TABLE 2-continued

Compounds of formula (Ia)

| No. | $R_1$ | $R_2$ | Ra | $R_3$ | q | phys. data |
|---|---|---|---|---|---|---|
| 2.117 | $OCF_3$ | $OCF_3$ | tetrazole-Me | OH | 1 | m.p. 125–135 |
| 2.118 | $CF_3$ | $CF_3$ | tetrazole-n-Prop. | OH | 0 | foam |
| 2.119 | $CF_3$ | $CF_3$ | tetrazole-n-Prop. | OH | 1 | m.p. 157–160 |
| 2.120 | $OCF_3$ | $OCF_3$ | tetrazole-n-Prop. | OH | 0 | resin |
| 2.121 | $OCF_3$ | $OCF_3$ | tetrazole-n-Prop. | OH | 1 | solid |
| 2.122 | $CF_3$ | F | NHCOO-i-Prop. | OH | 0 | foam |
| 2.123 | $OCF_3$ | $CF_3$ | tetrazole-$CH_3$ | OH | 0 | resin |
| 2.124 | $OCF_3$ | $CF_3$ | tetrazole-$CH_3$ | OH | 1 | m.p. 155–162 |
| 2.125 | $CF_3$ | $CF_3$ | —CH=$NOCH_3$ | OH | 0 | foam |
| 2.126 | $CF_3$ | $CF_3$ | —CH=$NOC_2H_5$ | OH | 0 | foam |
| 2.127 | $OCF_3$ | $OCF_3$ | —CH=$NOC_2H_5$ | OH | 0 | resin |
| 2.128 | $OCF_3$ | $CF_3$ | —CH=$NOC_2H_5$ | OH | 0 | resin |
| 2.129 | $OCF_3$ | $CF_3$ | —CH=$NOCH_3$ | OH | 0 | resin |
| 2.130 | $OCF_3$ | $CF_3$ | —CH=$NOC_2H_5$ | OH | 1 | foam |
| 2.131 | $OCF_3$ | $OCF_3$ | —CH=$NOC_2H_5$ | OH | 1 | foam |
| 2.132 | $CF_3$ | $CF_3$ | methoxy-chloro-pyridazine | OH | 0 | foam |

TABLE 2-continued
Compounds of formula
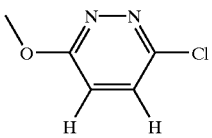
(Ia)
| No. | R₁ | R₂ | Ra | R₃ | q | phys. data |
|---|---|---|---|---|---|---|
| 2.133 | CF₃ | CF₃ | 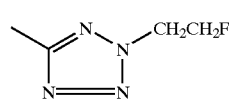 | OH | 1 | m.p. 159–163 |
| 2.134 | t-But | t-But | NHCOO-i-prop. | OH | 0 | foam |
| 2.135 | t-But | t-But | NHCOO-i-prop. | OH | 1 | m.p. 204–205 |
| 2.136 | CF₃ | CF₃ | 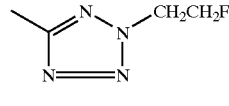 | OH | 0 | foam |
| 2.137 | CF₃ | CF₃ | 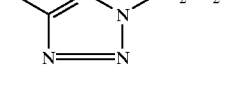 | OH | 0 | m.p. 156–164 |
| 2.138 | OCF₃ | CF₃ | 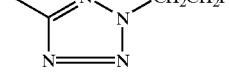 | OH | 0 | foam |
| 2.139 | OCF₃ | CF₃ | 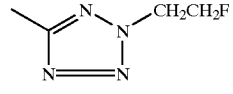 | OH | 1 | m.p. 167–169 |
| 2.140 | OCF₃ | OCF₃ | 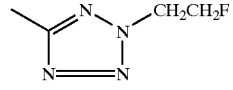 | OH | 0 | foam |
| 2.141 | OCF₃ | OCF₃ | 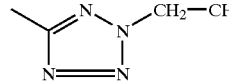 | OH | 1 | m.p. 165–167 |
| 2.142 | CF₃ | CF₃ | 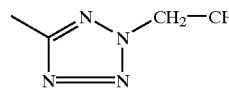 | OH | 0 | resin |
| 2.143 | CF₃ | CF₃ | 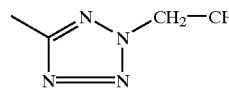 | OH | 1 | solid |
| 2.144 | CF₃ | CF₃ | 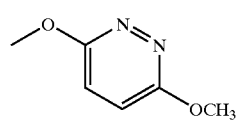 | OH | 0 | resin |

TABLE 2-continued

Compounds of formula (Ia)

| No. | R₁ | R₂ | Ra | R₃ | q | phys. data |
|---|---|---|---|---|---|---|
| 2.145 | CF₃ | CF₃ | 3,6-dimethoxy-pyridazinyloxy | OH | 1 | m.p. 164 |
| 2.146 | CF₃ | CF₃ | 2-methoxy-6-fluoro-pyridinyloxy | OH | 0 | resin |
| 2.147 | CF₃ | CF₃ | 2-methoxy-6-fluoro-pyridinyloxy | OH | 1 | m.p. 145–149 |
| 2.148 | OCF₃ | OCF₃ | 2-methoxy-6-fluoro-pyridinyloxy | OH | 0 | resin |
| 2.149 | OCF₃ | OCF₃ | 2-methoxy-6-fluoro-pyridinyloxy | OH | 1 | m.p. 128–134 |
| 2.150 | CF₃ | CF₃ | Phenyl | OH | 0 | foam |
| 2.151 | CF₃ | CF₃ | Phenyl | OH | 1 | m.p. 150–153 |

Formulation Examples (%=Percent by Weight)

Example F1: Emulsion concentrates

| | a) | b) | c) |
|---|---|---|---|
| active ingredient | 25% | 40% | 50% |
| calcium dodecylbenzenesulphonate | 5% | 8% | 6% |
| castor oil polyethylene glycol ether (36 mols EO) | 5% | — | — |
| tributyl phenol polyethylene glycol ether (30 mols EO) | — | 12% | 4% |
| cyctohexanone | — | 15% | 20% |
| xylene mixture | 65% | 25% | 20% |

Mixing of finely ground active ingredient and adjuvants results in an emulsion concentrate which is diluted with water to yield emulsions of the desired concentration.

Example F2: Solutions

| | a) | b) | c) | d) |
|---|---|---|---|---|
| active ingredient | 80% | 10% | 5% | 95% |
| ethylene glycol monomethyl ether | 20% | — | — | — |
| polyethylene glycol (MW 400) | — | 70% | — | — |
| N-methylpyrrolid-2-one | — | 20% | — | — |
| epoxidised coconut oil | — | — | 1% | 5% |
| petrol (boiling limits: 160–190°) | — | — | 94% | — |

Mixing of finely ground active ingredient and adjuvants results in a solution which is suitable for application in the form of fine droplets.

| Example F3: Granulates | | | | |
|---|---|---|---|---|
| | a) | b) | c) | d) |
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution sprayed onto the carrier mixture, and the solvent evaporated off under vacuum.

BIOLOGICAL EXAMPLES

Example B1

Effect on *Heliothis Virescens* Caterpillars

Young soya plants are sprayed with an aqueous emulsion spray mixture containing 400 ppm of active ingredient. After drying of the spray deposit, the soya plants are colonised with 10 first instar caterpillars of *Heliothis virescens* and placed in a plastic container. Six days later they are evaluated. The percentage reduction of the population and percentage reduction in feeding damage (% response) are determined by comparing the number of dead caterpillars and the extent of feeding damage on the treated plants with those on the untreated plants.

The compounds of table 2 show good efficacy against *Heliothis virescens* in this test. In particular, compounds 2.85, 2.86, 2.98, 2.99, 2.100 and 2.115 show efficacy of over 80%.

Example B2

Effect on *Plutella xylostella* Caterpillars

Young cabbage plants are sprayed with an aqueous emulsion spray mixture containing 400 ppm of active ingredient. After drying of the spray deposit, the cabbage plants are colonised with 10 third instar caterpillars of *Plutella xylostella* and placed in a plastic container. Three days later they are evaluated. The percentage reduction of the population and percentage reduction in feeding damage (% response) are determined by comparing the number of dead caterpillars and the extent of feeding damage on the treated plants with those on the untreated plants.

The compounds of table 2 show good efficacy against *Plutella xylostella*. In particular, compounds 2.85, 2.86, 2.94, 2.98, 2.99, 2.100 and 2.115 show efficacy of over 80%.

Example B3

Effect on *Diabrotica balteata* Larvae

Corn seedlings are sprayed with an aqueous emulsion spray mixture containing 400 ppm of active ingredient. After drying of the spray deposit, the corn seedlings are colonised with 10 second instar larvae of *Diabrotica balteata* and placed in a plastic container. Six days later they are evaluated. The percentage reduction of the population (% response) is determined by comparing the number of dead larvae on the treated plants with those on the untreated plants.

The compounds of table 2 show good efficacy against *Diabrotica balteata* in this test. In particular, compounds 2.85, 2.86, 2.99 and 2.100 show efficacy of over 80%.

I claim:
1. Compound of formula

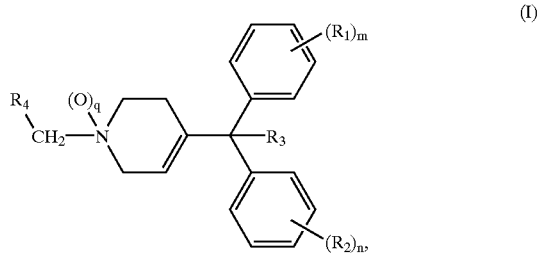

wherein
$R_1$ and $R_2$, independently of one another, are halogen, $C_1$–$C_6$-alkyl, $C_3$–$C_6$-cycloalkyl, halogen-$C_1$–$C_6$-alkyl, halogen-$C_3$–$C_6$-cycloalkyl, $C_2$–$C_4$-alkenyl, $C_2$–$C_4$-alkinyl, halogen-$C_2$–$C_4$-alkenyl, halogen-$C_2$–$C_4$-alkinyl, $C_1$–$C_6$-alkoxy, halogen-$C_1$–$C_6$-alkoxy, $C_2$–$C_6$-alkenyloxy, $C_2$–$C_6$-alkinyloxy, halogen-$C_2$–$C_6$-alkenyloxy, halogen-$C_2$–$C_6$-alkinyloxy, —$SF_5$, —C(=O)N($R_5$)$_2$, —O—C(=O)N($R_5$)$_2$, —CN, —$NO_2$, —S(=O)$_2$N($R_5$)$_2$, —S(=O)$_p$—$C_1$–$C_6$-alkyl, —S(=O)$_p$-halogen-$C_1$–$C_6$-alkyl, —O—S(=O)$_p$—$C_1$–$C_6$-alkyl, —O—S(=O)$_p$-halogen-$C_1$–$C_6$-alkyl, phenyl, benzyl, phenoxy or benzyloxy, wherein each of the phenyl, benzyl, phenoxy or benzyloxy radicals is either unsubstituted or mono- to penta-substituted in the aromatic ring, independently of each other, by substituents selected from the group consisting of halogen, cyano, $NO_2$, $C_1$–$C_6$-alkyl, halogen-$C_1$–$C_6$-alkyl, $C_1$–$C_6$-alkoxy and halogen-$C_1$–$C_6$-alkoxy;
$R_3$ is hydrogen, OH, halogen, $C_1$–$C_6$-alkoxy, or —O—C(=O)—$C_1$–$C_6$-alkyl;
$R_4$ is phenyl, which is mono- to penta-substituted, independently of each other, by substituents selected from the group consisting of halogen, cyano, $NO_2$, $C_1$–$C_6$-alkyl, $C_3$–$C_8$-cycloalkyl, $C_3$–$C_8$-cycloalkyl-$C_1$–$C_6$-alkyl, halogen-$C_1$–$C_6$-alkyl, $C_1$–$C_6$-alkoxy, $C_3$–$C_8$-cycloalkoxy, $C_3$–$C_8$-cycloalkoxy-$C_1$–$C_6$-alkyl, $C_3$–$C_8$-cycloalkyl-$C_1$–$C_6$-alkoxy, halogen-$C_1$–$C_6$-alkoxy, $C_2$–$C_4$-alkenyl, $C_2$–$C_4$-alkinyl, $C_2$–$C_6$-alkenyloxy, $C_2$–$C_6$-alkinyloxy, —$NR_6$—C(=O)—O—$C_1$–$C_6$-alkyl, —$NR_6$—C(=O)—O-halogen-$C_1$–$C_6$-alkyl, —C($R_7$)=N—W—$R_8$,
the two $R_5$ independently of one another, are hydrogen or $C_1$–$C_6$-alkyl;
$R_6$ is hydrogen, $C_1$–$C_6$-alkyl or benzyl;
$R_7$ is halogen, $C_1$–$C_6$-alkyl, $C_3$–$C_8$-cycloalkyl, $C_3$–$C_8$-cycloalkyl-$C_1$–$C_6$-alkyl, halogen-$C_1$–$C_6$-alkyl, $C_1$–$C_6$-alkoxy, $C_3$–$C_8$-cycloalkoxy, $C_3$–$C_8$-cycloalkoxy-$C_1$–$C_6$-alkyl, halogen-$C_1$–$C_6$-alkoxy, —NH($C_1$–$C_6$-alkyl) or —N($C_1$–$C_6$-alkyl)$_2$;
$R_8$ is hydrogen, $C_1$–$C_6$-alkyl, $C_3$–$C_8$-cycloalkyl, $C_3$–$C_8$-cycloalkyl-$C_1$–$C_6$-alkyl, halogen-$C_1$–$C_6$-alkyl or —C(=O)—$C_1$–$C_6$-alkyl;
m is 0, 1, 2, 3, 4 or 5;
n is 0, 1, 2, 3, 4 or 5;
p is 0, 1 or 2;
q is 0 or 1
W is O or NH or N—$C_1$–$C_6$-alkyl;
and, the E/Z isomers, E/Z isomeric mixtures and/or tautomers thereof, each in free form or in salt form.
2. A compound of formula (I) according to claim 1, in free form.

3. A compound of formula (I) according to one of claims 1 or 2, wherein $R_1$ and $R_2$, independently of each other, are halogen, $C_1$–$C_2$-alkyl, $C_3$–$C_6$-cycloalkyl, halogen-$C_1$–$C_2$-alkyl, $C_1$–$C_2$-alkoxy, halogen-$C_1$–$C_2$-alkoxy, —C(=O)N(CH$_3$)$_2$, —CN or —NO$_2$.

4. A compound of formula (I) according to one of claims 1 to 3, in which $R_3$ is hydrogen, OH, halogen or $C_1$–$C_6$-alkoxy.

5. An insecticidal and acaricidal composition comprising one or more compounds of formula (I) according to claim 1 as active ingredient, either in free form or in the form of an agrochemically acceptable salt, and one or more adjuvants.

6. A method for the control of insects and representatives of the order Acarina in which a compound of formula (I) according to claim 1 as the active ingredient is applied, in free form or in the form of an agrochemically acceptable salt, to insects and representatives of the order Acarina, or their habitat, in an amount of 1 to 2000 g per hectare.

* * * * *